Dec. 24, 1946. H. C. SWIM Plant Pat. 719
ROSE PLANT
Filed Jan. 3, 1946
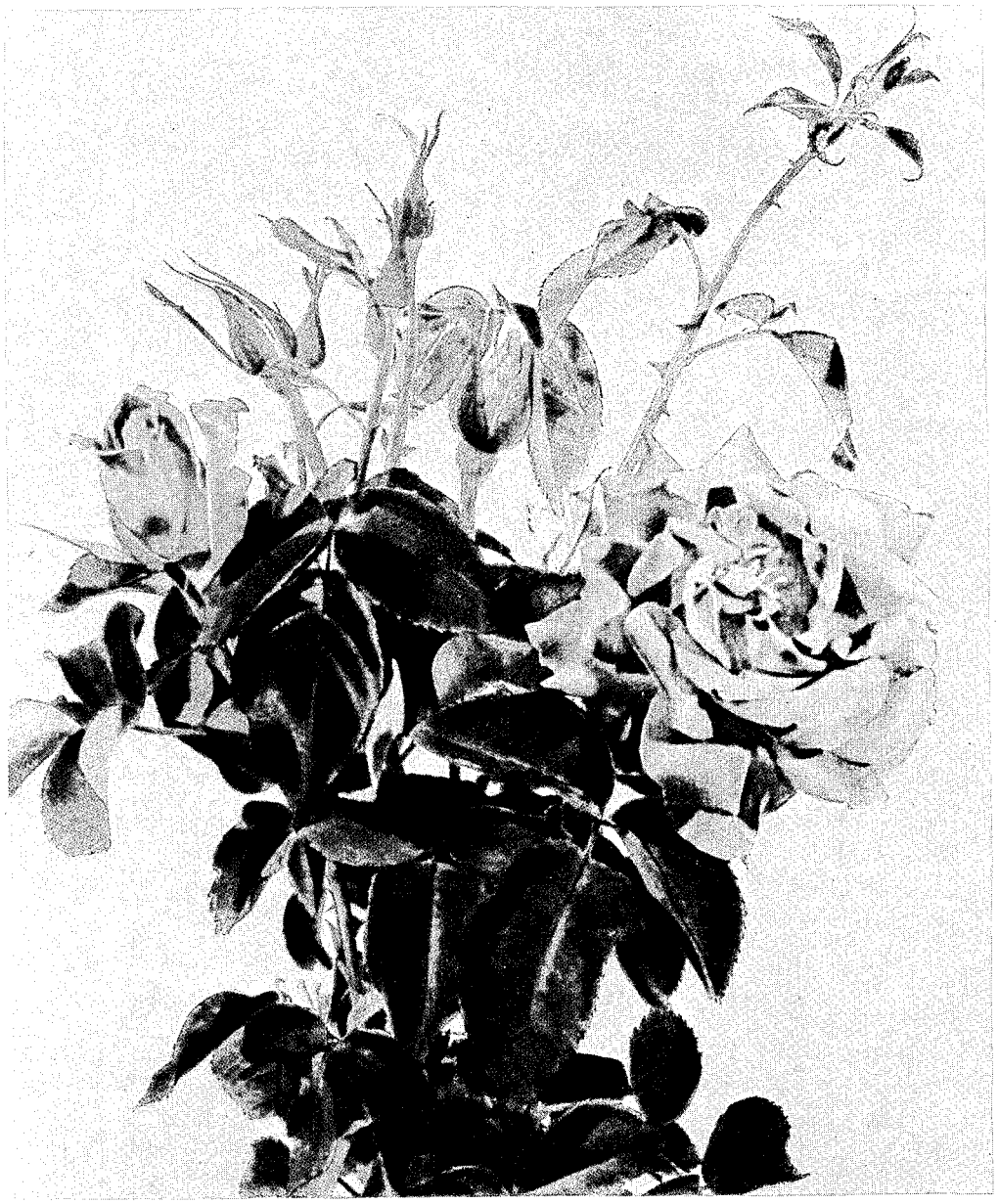
Inventor
H. C. Swim
By Robert Cobb
Attorney Patented Dec. 24, 1946

Plant Pat. 719

UNITED STATES PATENT OFFICE

719

ROSE PLANT

Herbert C. Swim, Ontario, Calif., assignor to Armstrong Nurseries, Inc., Ontario, Calif., a corporation of California Application January 3, 1946, Serial No. 638,823

1 Claim. (Cl. 47—61)

The present invention relates to a new and distinct variety of rose plant, originated by the crossing of the varieties "Charlotte Armstrong" and "Piccaninny," thereby resulting in the production of a rose, which, in the combination of its most outstanding characters of foliage and flower color, resembles no other rose variety of which I am aware.

Its dominant distinctions and resemblances to others may be briefly summarized for convenience as follows:

(1) Plant: Very vigorous, upright; free-branching with relatively few thorns. Cane—distinctive, lighter green for red-flower class of rose.

(2) Foliage: Very large, abundant, flat, with high gloss and moderate resistance to mildew.

(3) Flower: Distinctive color, particularly in newly opened flowers where the general color effect is a light shade of red, blending with a Magenta shade on the tips of the petals on the inner surface. In form—flat flower, composed of very broad, outer petals and moderately broad inner petals, displaying a tendency in the petals to close at night instead of opening as normally expected, this trait somewhat delimiting the use of this variety for cut flower purposes, but in nowise affecting its utility for garden decoration.

(4) Differences from and resemblances to parents: No visual resemblance to "Charlotte Armstrong" except in minor, inconspicuous points, such as a yellow base to petals and an occasional vegetative streak in one or more of the outer petals. It differs widely from "Piccaninny" in color and petalage, since "Piccaninny" is very dark red (near darkest shade of Maroon, Wilson, Plate 1030, page 185), and further this parent is a single rose with only five to six petals and of a size roughly one-half that of the new variety. The latter further resembles its pollen parent in respect to the abundance and glossiness of foliage which is in this new rose, however, larger and more mildew resistant. Resemblance continues in relation to the pollen parent as to habit of growth and vigor and slightly as to appearance of the canes and branches.

These and other characteristics of distinction will be more specifically referred to hereinafter and in the accompanying drawing wherein is shown specimens of the foliage (young and mature) and of the blooms in the different stages of development of buds, half-opened and fully-opened flowers.

Asexual reproduction shows that these characteristics hold true through succeeding propagations.

The following is a detailed description of the new variety, all references to color being in accordance with the R. F. Wilson's Horticultural Colour Chart, except where indicated to be in accordance with Ridgway's Color Standard and Nomenclature:

Type: Tall; bush; outdoor; seedling; for garden decoration and limited use for cut flowers.

Class: Hybrid tea.

Breeding: Seedling.

*Seed parent.*—"Charlotte Armstrong" (Pl. Pat. No. 455).

*Pollen parent.*—"Piccaninny."

Propagation: By budding, the only method tried so far.

*Flower*

Locality where grown: Ontario, California.

Flowers borne: Singly, three and four and sometimes six to stem; in irregular cluster; on normally strong, medium length stems.

Quantity of bloom: Free; outdoors.

Continuity: Continuous during growing season.

Fragrance: Moderate; spicy.

Bud:

*Peduncle.*—Medium length; medium heavy; erect; medium rough; numerous gland-tipped cilia and prickles. *Color*—near Morocco Red, Plate I (Ridgway), on side exposed to sun; to near Grape Green, Plate XLI (Ridgway), on shaded side.

*Before calyx breaks.* — *Size* — medium. *Form*—medium pointed; with foliaceous appendages and glandular bloom, on the surface of the bud; with slender, much cut foliaceous parts extending beyond the tip of the bud equal to one-half or more of its length.

*As calyx breaks.*—*Color*—Indian Lake, Plate 826, page 170, to near Cardinal Red, Plate 822, page 168, at base. (In some specimens this color is Blood Red, page 166.) *Inner surface*—with fine, woolly tomentum. Margins have stipitate glands and woolly tomentum when an adjacent sepal does not cover margin; if margin is covered by adjacent sepal, it has only woolly tomentum.

*As first petal opens.*—*Size*—medium. *Form*—short; pointed to urn shape. *Color*—outside: Currant Red, Plate 821/2, page 167; inside: Cardinal Red, Plate 822 page 168, with Chrysanthemum Crimson, Plate 824, page 169, shading.

*Opening.*—Opens up well.

Bloom:

*Size.*—When fully open, medium to large; 3½ inches to 4½ inches.

*Petalage.*—Double but the stamens not hidden except in the more double flowers, the stamens may be hidden at times by the petals; from 18 to 28 petals plus 3 to 7 petaloids; arranged irregularly.

*Form.*—High center at first; becoming open; petals remaining at first loosely rolled outward; becoming later, at maturity, loosely flat with reflexed tips during daylight. Flowers tend to close at night. In cool weather, open flowers do not become flat because petals tend to stand apart with center petals nearly erect.

Petals: Medium thick; moderately leathery in cool weather; but soft in hot weather; with inside velvety and outside satiny.

*Shape.*—Outside—obovate with apex flat. Intermediate—obovate; slightly scalloped with apex flat, with one to two notches. Inside—near cuneate; slightly scalloped with apex flat with one to two notches.

*Color.*—Colors may be modified by being shaded with other colors.

This description of a newly opened flower was made from a rose grown outdoors in the month of October, 1945, at Ontario, California, in cool weather:

*Color.*—*Outside petal*—outside surface: Crimson, Plate 22/2, page 22, with Chrome Yellow, Plate 605, page 144, at base; inside surface: Rose Red, Plate 724, page 158, with Chrome Yellow, Plate 605, page 144, at base. *Intermediate petal*—outside surface: Cherry, Plate 722/3, page 157, with small sector of Chrome Yellow, Plate 605, page 144, at base; inside surface: near Currant Red, Plate 821/3, page 167, with Chrome Yellow, Plate 605, at page 144, at base. *Inner petal*—outside surface: Cherry, Plate 722/3, page 157, with Chrome Yellow, Plate 605, page 144, at base; inside surface—near Currant Red, Plate 821/1, page 167, with Chrome Yellow, Plate 605, page 144, at base.

This description was made from a rose that was open for three days outdoors in the month of October, 1945, at Ontario, California, in cool weather:

*Outside petal.*—Outside surface—near Phlox Pink, Plate 625, page 77, with Magenta, Plate 27/1, page 27, shading, with small sector of Amber Yellow, Plate 505/1, page 132, at base. Inside surface—near Tyrian Purple, Plate 727/1, page 159, with Amber Yellow, Plate 505, page 132, at base.

*Inside petal.*—Outside surface—near Crimson, Plate 22/1, page 22, with Magenta, Plate 27/2, page 27, shading; near Amber Yellow, Plate 505/1, page 132, at base. Inside surface—near Rose Red, Plate 724/3, page 158; near Amber Yellow, Plate 505, page 132, at base.

*General color effect.*—Newly opened flower—near Currant Red, Plate 821/3, page 167, with Magenta, Plate 27/2, page 27, shading on outer surfaces. Three days open— near Rose Red, Plate 724/3, page 158, with Magenta, Plate 27/2, page 27, shading.

*Behavior.*—Drop off cleanly; fading slightly purple; affected by hot weather by fading to a blue-purple shade in hot weather.

*Flower longevity.*—On bush in garden—3 to 4 days in October. Cut roses grown indoors, kept at living room temperatures, three days in October.

*Reproductive organs*

Stamens: Medium to many; arranged regularly about pistils, mixed with petaloids.

Filaments: Medium to long; from 5 to 12 mm. in length. *Color*—near Fire Red, Plate 15/2, page 15. Most with anthers.

Anthers: Medium size; all open at once approximately. *Color*—near Barium Yellow, Plate 503/2, page 131, with Amber Yellow, Plate 505, page 132, at margin.

Pollen: Moderate. *Color*—near Orange Buff, Plate 507, page 133.

Pistils: Medium to many, approximately 55 in number.

Styles: Uneven; short to medium; medium heavy; loosely bunched. *Color*—near Blood Red, Plate 820/2, page 166, becoming near Sap Green, Plate 62/2, page 62, at base.

Stigma: Grayish white, somewhat translucent.

Ovaries: All enclosed in calyx.

Hips: Globular. *Color*—mature hips near Orange Rufous, Plate II (Ridgway), on sunny side, to a Pyrite Yellow, Plate IV (Ridgway), on shaded side. Moderately smooth upper part; glandular near base. Walls—thick, fleshy.

Sepals: Falling before maturity; moderately short, recurved. Sepals from flower open one day; inside: near Vetiver Green, Plate XLVII (Ridgway); outside: near Rainette Green, Plate XXXI (Ridgway), blotched with Vandyke Red, Plate XIII (Ridgway).

Seeds: Many, approximately 20 seeds; medium to large.

*Plant*

Foliage:

*Leaves.*—Compound of five to seven leaflets; abundant; very large; heavy; glossy.

*Leaflets.*—Shape—ovate with apex acute. Base—obtuse. Margin—doubly serrate.

*Color.* — *Mature* — upper surface: Parsley Green, Plate 00962/1, page 193; under surface—Lavender Green, Plate 000761, page 196. *Young*—upper surface: between Claret Brown, Plate I (Ridgway), and Brick Red, Plate XIII (Ridgway), but glossy; under surface: between Acajou Red, Plate XIII (Ridgway), and Vandyke Red, Plate XIII (Ridgway).

*Rachis.* — Medium heavy. Upper side grooved with stipitate glands. Under side moderately prickly with stipitate glands.

*Stipules.*—Medium long, 12 mm.; medium wide; with medium long points, turning out at an angle of more than 45°, recurved toward the stem.

*Disease.*—Moderate resistant to mildew.

Growth:

*Habit.*—Bushy; upright; much branched.

*Growth.*—Vigorous.

*Canes.*—Medium heavy.

*Main stems.*—Deep Grape Green, Plate XLI (Ridgway). *Large Prickles*—several; medium to large; slightly hooked downward; with medium, somewhat narrow, base.

Color—near Rood's Brown, Plate XXVIII (Ridgway). Near Burnt Umber, Plate XXVIII (Ridgway), at base. *Small prickles*—few. Color—near Rood's Brown, Plate XXVIII (Ridgway), to near Burnt Umber, Plate XXVIII (Ridgway), at base. *Hairs*—none.

*Branches*—Near Asphodel Green, Plate XLI (Ridgway). *Large prickes*—several; medium length; hooked downward; with slightly medium narrow base. Color—near Straw Yellow, Plate XVI (Ridgway). *Small prickles*—several. Color — near Auburn, Plate II (Ridgway). *Hairs*—none; few stipitate glands on branches.

*New shoots.*—Near Garnet Brown, Plate I (Ridgway). *Large prickles*—several; medium length; hooked downward; with slightly medium narrow base. Color—near Rhodonite Red, Plate 0022, page 188. Somewhat translucent. *Small prickles*—several. Color—near Rhodonite Red, Plate 0022, page 188; somewhat translucent. *Hairs*—none, but some stipitate glands on new shoots.

I claim:

A new and distinct variety of rose plant characterized as to novelty by its very vigorous, upright, free branching habit of growth, with relatively few thorns; distinctive color of its canes; abundant, glossy, relatively large foliage, resistant to mildew; and form, size and red coloring of its blooms, together with the tendency of said blooms to close at night, substantially as shown and described.

HERBERT C. SWIM.